United States Patent [19]

Chan

[11] 4,264,598

[45] Apr. 28, 1981

[54] 1,3,5-TRIALKYNYL-HEXAHYDRO-1,3,5-TRIAZINE

[75] Inventor: David C. K. Chan, Petaluma, Calif.

[73] Assignee: Chevron Research Company, San Francisco, Calif.

[21] Appl. No.: 115,589

[22] Filed: Jan. 28, 1980

[51] Int. Cl.$^3$ ............... C07D 251/04; A61K 31/53
[52] U.S. Cl. ........................... 424/249; 544/180
[58] Field of Search .................. 544/180; 424/249

[56] References Cited

U.S. PATENT DOCUMENTS

| 2,889,277 | 6/1959 | Hughes et al. | 544/180 |
| 3,163,647 | 12/1964 | Schaefer et al. | 544/180 |
| 3,755,590 | 8/1973 | Brooks et al. | 424/249 |
| 3,840,661 | 10/1974 | Waldstein | 544/215 |

OTHER PUBLICATIONS

Demare et al., Chem. Abst., 119670U, vol. 78.

Primary Examiner—Henry R. Jiles
Assistant Examiner—Jane T. Fan
Attorney, Agent, or Firm—D. A. Newell; T. G. DeJonghe; R. J. Suyat

[57] ABSTRACT

1,3,5-Trialkynyl-hexahydro-1,3,5-triazines have fungicidal activity.

11 Claims, No Drawings

1,3,5-TRIALKYNYL-HEXAHYDRO-1,3,5-TRIAZINE

BACKGROUND OF THE INVENTION

Waldstein discloses fungicidal 1,3,5-(beta-hydroxyethyl)hexahydro-s-triazine bromine adducts in U.S. Pat. No. 3,840,661.

DESCRIPTION OF THE INVENTION

Compounds of the invention are represented by the formula (I):

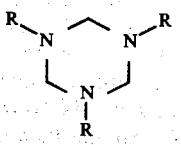

wherein R is an alkynyl group of 2 to 12 carbon atoms or an alkynyl-substituted cycloalkyl group of 5 to 12 carbon atoms.

Representative R groups are ethynyl, propargyl, but-2-ynyl, but-3-ynyl, 1-methyl-propargyl, hex-3-ynyl, 4,4-di-methylpent-2-ynyl, dec-5-ynyl, dodec-6-ynyl, 2-ethynyl-cyclo-pentyl, 4-propargyl-cyclohexyl, 1-ethynyl-cyclooctyl, 1-ethynyl-cyclohexyl, 1-propargyl-cycloheptyl.

Preferably R is alkynyl of 2 to 6 carbon atoms and alkynyl-substituted cycloalkyl of 5 to 8 carbon atoms. More preferably, R is alkynyl-substituted cycloalkyl of 5 to 8 carbon atoms.

Most preferably R is 1-ethynyl-cyclohexyl.

The compounds of the invention may be prepared by condensing an amine $RNH_2$ with paraformaldehyde, $(CH_2O)_x$, in an inert organic diluent. The condensation reaction may be performed using a slight molar excess of paraformaldehyde. The reaction may be conducted at 40°–130° C., preferably at 80°–115° C. The reaction may be conducted in the presence of a slight amount of a tertiary amine.

UTILITY

The compounds of the invention are useful for controlling fungi, particularly plant fungal infections. However, some fungicidal compositions of the invention may be more fungicidally active than others against particular fungi. For example, the activity of the preferred compounds of the invention is highly specific for certain fungal diseases such as late blights, e.g., *Phytophthora infestans* (tomatoes and potatoes), and early blights, e.g., *Alternaria*.

The compounds of the invention are particularly useful fungicides because they cure established fungal infections. This permits economical use of the fungicides of the invention, because they need not be applied to plants unless fungal infection actually occurs. Thus, a preventative program of applying fungicides against potential fungal infection is not necessary.

When used as fungicides, the compounds of the invention are applied in fungicidally effective amounts to fungi and/or their habitats, such as vegetative hosts and nonvegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, the example: the aryl and alkylaryl sulfonates and their sodium salts, alkylamide sulfonates, including fatty methyl taurides; alkylaryl polyether alcohols, sulfated higher alcohols and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLE 1—TOMATO LATE BLIGHT

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a small amount of a nonionic emulsifier. The sprayed plants were then inoculated one day later with the organism, placed in an environmental chamber and incubated at 66°–68° F. and 100% relative humidity for at least 16 hours. Following the incubation, the plants were maintained in a greenhouse at 60–80% relative humidity for approximately 7 days. The percent disease control provided by a given test compound was based on the percent disease reduction relative to untreated check plants. The results are tabulated in Table I. In Table I, the test concentration is 250 ppm unless otherwise indicated by the figures in parentheses.

EXAMPLE 2—CELERY LATE BLIGHT

The celery late blight tests were conducted using celery (Utah) plants 11 weeks old. The celery late blight organism was *Septoria apii*. The celery plants were sprayed with solutions of the candidate toxicant mixed with acetone, water and a nonionic emulsifier. The plants were then inoculated with the organism and placed in an environmental chamber and incubated at 66°–68° F. in 100% relative humidity for an extended period of time (approximately 48 hours). Following the incubation the plants were allowed to dry and then were maintained at a 60–80% relative humidity for approximately 14 days. The percent disease control provided by a given candidate toxicant is based on the percent disease reduction relative to untreated check plants. The results are reported in Table I.

EXAMPLE 3—TOMATO EARLY BLIGHT

Compounds of the invention were tested for the control of the Tomato Early Blight organism, *Alternaria solani conidia*. Tomato (variety Bonny Best) seedlings of 6 to 7 weeks old were used. The tomato plants were sprayed with a 250-ppm solution of the test compound in an acetone-and-water solution containing a small amount of a nonionic emulsifier. The sprayed plants were inoculated one day later with the organism, dried and maintained at 60–80% relative humidity for about 12 days. Percent disease control was based on the percent disease development on untreated check plants. The compounds tested and the results are tabulated in Table I.

EXAMPLE 4—POWDERY MILDEW

The powdery mildew test was made using bean seedlings (var. Bountiful) with well-developed primary leaves. The pathogen was *Erysiphe polygoni*. The bean seedlings were sprayed with a 250-ppm solution of the test compound in an acetone-water mixture containing a nonionic emulsifier. The treated plants were inoculated one day after spray application of the test compound with the pathogen. The plants were then maintained in a greenhouse at a 60–80% relative humidity and at a temperature of 68°–70° F. The rate of infection on the leaves was made after about 10 days. The percent disease control provided by a given test compound was based on the disease reduction relative to untreated check plants. The results are reported in Table I.

EXAMPLE 5—LEAF RUST

The leaf-rust was made using pinto beans. The pathogen was *Uronyces phaseoli tipica*. The pinto-bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68°–70° F. The plants were then removed from the chamber, allowed to dry, and then maintained in a greenhouse at a 60–80% relative humidity. The rate of infection on the leaves was made after about 14 days. The percent disease control provided by a given test compound was based on the disease reduction relative to untreated check plants. The results are reported in Table I.

EXAMPLE 6—PREPARATION OF 1,3,5-TRI(1'-ETHYNYLCYCLOHEXYL)-HEXAHYDRO-1,3,5-TRIAZINE

To a solution of 1-ethynyl-cyclohexylamine (90 g) and paraformaldehyde (30 g) in 125 ml benzene was added 1 ml of 25% triethylamine in methanol. The mixture was refluxed under a Dean-Stark trap. After one hour about 20 ml of water was trapped, the mixture was cooled and stripped. The residue was washed and crystallized (hexane/benzene) to yield the title product (28 g) (Compound 1).

| Analysis: | Calc. | Fd |
|---|---|---|
| C | 79.95 | 80.15 |
| H | 9.69 | 9.75 |
| N | 10.36 | 10.16 |

Using the above procedure with 1,1-dimethylpropargylamine, the compound 1,3,5-(1',1'-dimethyl-propargyl)-hexahydro-1,3,5-triazine (Compound 2) was prepared.

| Analysis: | Calc. | Fd |
|---|---|---|
| C | 75.78 | 75.03 |
| H | 9.54 | 9.51 |
| N | 14.73 | 15.17 |

TABLE I

| | FUNGICIDAL EFFICACY, % CONTROL | | | | |
|---|---|---|---|---|---|
| No. | TLB | LR | PM | CLB | TEB |
| 1 | 100 | 0 | 37 | 74 | 100 |
| 2 | 0 | 0 | 0 | 27 | 0 |

What is claimed is:

1. A compound of the formula

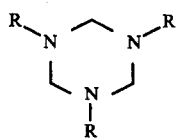 (I)

wherein R is an alkynyl group of 2 to 12 carbon atoms or a cycloalkyl group of 5 to 12 carbon atoms substituted with an alkynyl group of 2 to 3 carbon atoms.

2. The compound according to claim 1 wherein R is an alkynyl-substituted cycloalkyl group of 6 to 12 carbon atoms.

3. The compound according to claim 2 wherein R is the group

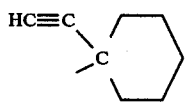

4. A compound according to claim 1 wherein R is an alkynyl group of 2 of 12 carbon atoms.

5. The compound according to claim 4 wherein R is 1,1-dimethylpropargyl.

6. A method of controlling fungi which comprises contacting said fungi with a fungicidally effective amount of a compound of the formula defined in claim 1.

7. The method of claim 6 wherein R is an alkynyl-substituted cycloalkyl group of 5 to 12 carbon atoms.

8. The method of claim 7 wherein R is the group

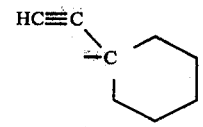

9. A fungicidal composition comprising a biologically inert carrier and a fungicidally effective amount of a compound of the formula defined in claim 1.

10. The composition of claim 9 wherein R is an alkynyl-substituted cycloalkyl group of 5 to 12 carbon atoms.

11. The composition of claim 10 wherein R is the group

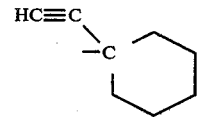

* * * * *